United States Patent [19]

Holzhauer et al.

[11] Patent Number: 5,254,719

[45] Date of Patent: Oct. 19, 1993

[54] PROCESS FOR PREPARING PURIFIED DIMETHYL NAPHTHALENEDICARBOXYLATE

[75] Inventors: Juergen K. Holzhauer, Naperville; David A. Young, Warrenville, both of Ill.

[73] Assignee: Amoco Corporation, Chicago, Ill.

[21] Appl. No.: 708,492

[22] Filed: May 31, 1991

[51] Int. Cl.$^5$ .............................................. C07C 67/54
[52] U.S. Cl. ...................................... 560/78; 560/77; 562/412; 562/486; 562/488
[58] Field of Search .................. 560/78; 562/488, 486, 562/416

[56] References Cited

U.S. PATENT DOCUMENTS 3,485,867 12/1969 Jackson ................................ 560/78
5,095,135 3/1992 Yamada et al. ..................... 560/100

FOREIGN PATENT DOCUMENTS 50-116461 9/1975 Japan .
50-83362 11/1975 Japan .
62-290722 12/1987 Japan .

Primary Examiner—Paul F. Shaver
Assistant Examiner—Vera C. Clarke
Attorney, Agent, or Firm—Thomas E. Nemo; Wallace L. Oliver; Frank J. Sroka

[57] ABSTRACT

A process for preparing purified dimethyl-2,6-naphthalenedicarboxylate by the esterification of 2,6-naphthalenedicarboxylic acid is disclosed, and which process provides for the efficient removal of residual oxidation catalyst metals from the dimethyl-2,6-naphthalenedicarboxylate and efficient removal of particulate contaminants.

11 Claims, No Drawings

PROCESS FOR PREPARING PURIFIED DIMETHYL NAPHTHALENEDICARBOXYLATE

FIELD OF THE INVENTION

This invention relates generally to a process for preparing purified dimethyl naphthalenedicarboxylate containing low levels of organic impurities, low color, and low levels of particulate contaminants. More particularly, this invention relates to a process for preparing purified dimethyl-2,6-naphthalenedicarboxylate by the esterification of 2,6-naphthalenedicarboxylic acid with methanol, and which process provides for the efficient elimination of residual oxidation catalyst metals contained in the 2,6-naphthalenedicarboxylic acid used for making dimethyl-2,6-naphthalenedicarboxylate.

BACKGROUND OF THE INVENTION

The diesters of naphthalenedicarboxylic acids are useful for preparing a variety of polymeric materials such as polyesters or polyamides. One particularly useful diester is dimethyl-2,6-naphthalenedicarboxylate (DM-2,6-NDC). Dimethyl-2,6-naphthalenedicarboxylate, for example, can be condensed with ethylene glycol to form poly(ethylene-2,6-naphthalate) (PEN), a high performance polyester material. Fibers and films made from PEN have considerably improved strength and superior thermal properties relative to, for example, poly(ethyleneterephthalate). For this reason, PEN is an exceptional material for preparing commercial articles such as thin films which can be used, for example, for the manufacture of magnetic recording tape and electronic components. Additionally, because of its superior resistance to gas diffusion, and particularly to the diffusion of carbon dioxide, oxygen and water vapor, films made from PEN are useful for manufacturing food containers, especially the so-called "hot fill" food containers. PEN is also useful for preparing high strength fibers which can be used to manufacture, for example, tire cord.

In order to prepare high quality PEN suitable for commercial use, it is necessary to start with purified DM-2,6-NDC. The purified DM-2,6-NDC must be low in color, substantially free of organic and inorganic impurities, and low in particulate matter.

DM-2,6-NDC is most readily prepared by the esterification of 2,6-naphthalenedicarboxylic acid (2,6-NDA) with methanol. The 2,6-NDA is conveniently prepared by the oxidation of a 2,6-dialkyl- or 2-alkyl-6-acyl naphthalene compound using molecular oxygen and catalyzed by a catalyst comprising cobalt, manganese and bromine components. During this oxidation reaction impurities such as 6-formyl-2-naphthoic acid (FNA), trimellitic acid (TMLA) and various brominated compounds are produced. Although in some instances it would be desirable to use 2,6-NDA directly for the preparation of PEN, however, because of its high melting point (>300° C. with decomposition) and extremely low solubility in ordinary solvents, 2,6-NDA is extremely difficult to purify to acceptable levels by standard purification techniques such as distillation and recrystallization. These difficulties in purifying 2,6-NDA are partially overcome by converting 2,6-NDA to its dimethyl ester, DM-2,6-NDC. DM-2,6-NDC can be distilled and it can be recrystallized from solvents such as methanol or from one or more aromatic solvents. However, even though DM-2,6-NDC can be purified by treatments such as distillation or recrystallization, purifying DM-2,6-NDC to a purity acceptable for use in the aforementioned manufactured articles remains a problem in the art. For example, the FNA produced during the oxidation of dialkylnaphthalene is incorporated (as a methyl ester) into DM-2,6-NDC during the esterfication of 2,6-NDA and is very difficult to remove or reduce to acceptable low levels. In particular, cobalt and manganese oxidation catalyst metals used for the preparation of 2,6-NDA are also typically carried over into the esterification reaction as impurities. This is because a certain amount of the oxidation catalyst metal is complexed tightly to TMLA and other oxidation by-products and is not removed in the oxidation mother liquor when the oxidation mother liquor is separated from the solid 2,6-NDA. Catalyst metals cause problems in the downstream operations used for purifying the DM-2,6-NDC by, for example, causing a thickening of the distillation bottoms and plugging of the distillation column. These catalyst metals must be removed prior to the distillation of DM-2,6-NDC.

Finally, particulate contamination in the DM-2,6-NDC must be eliminated or reduced to very low levels. Particulate contamination in the DM-2,6-NDC causes particulate contamination in PEN made from the DM-2,6-NDC. These particulate contaminants render the PEN unsuitable for manufacturing the thin, high-strength film used to prepare, for example, recording tape. These particulate impurities, which range in size down to below 1.5 microns, can arise from a variety of sources. For example, they may be oxidation catalyst particles. They may also be derived from filtering and drying operations where DM-2,6-NDC is dissolved in a solvent, recrystallized, separated from the recrystallization mother liquor by filtration and dried to remove excess solvent. Inevitably, a considerable amount of particulates contaminate the DM-2,6-NDC product in these processes. Regardless of the source, particulate contamination in the DM-2,6-NDC product is undesirable.

Processes for manufacturing and purifying DM-2,6-NDC have been disclosed. Japanese Kokai Patent No. Sho 50-116461, for example, discloses a process for preparing DM-2,6-NDC wherein crude DM-2,6-NDC from the esterification of 2,6-NDA with methanol is distilled and then crystallized from methanol. This process is taught as being superior to one where the crystallization from methanol precedes the distillation. However, the Japanese Kokai Patent No. Sho 50-116461, although disclosing a process for preparing DM-2,6-NDC from 2,6-NDA by reaction with methanol, does not disclose a means for eliminating oxidation catalyst metals from DM-2,6-NDC prior to downstream distillation procedures. Additionally, this Kokai patent teaches that it is essential to recrystallize the DM-2,6-NDC subsequent to a distillation step in order to prepare DM-2,6-NDC with acceptable color. However, this order of the purification steps does not provide for low levels of particulates in the final DM-2,6-NDC product that is required for some of the aforementioned uses of DM-2,6-NDC.

Japanese Kokai Patent No. Sho 50-83362 discloses the use of sulfuric acid as a catalyst for the esterification of 2,6-NDA in a temperature range of 120°–220° C. and in the presence of a naphthalene derivative. However, it does not disclose the use of sulfuric acid to remove oxidation catalyst metals from DM-2,6-NDC, or the presence of oxidation catalyst metals in 2,6-NDA. Further, this Kokai Patent does not disclose the necessity of distilling DM-2,6-NDC as a final purification step to prepare DM-2,6-NDC having low particulate contamination.

The art needs a process for the preparation of DM-2,6-NDC having suitably low color, low levels of inorganic and organic impurities and low levels of particulate contaminants. The art also needs a process for efficiently removing residual cobalt and manganese oxidation catalyst metals from the DM-2,6-NDC. The present invention provides such a process.

SUMMARY OF THE INVENTION

Provided is a process for preparing purified dimethyl-2,6-naphthalenedicarboxylic from 2,6-naphthalenedicarboxylic acid, wherein the 2,6-naphthalenedicarboxylic acid is prepared by the liquid phase oxidation of a 2,6-dialkyl- or 2-alkyl-6-acyl naphthalene compound using a catalyst comprising cobalt, manganese and bromine components, which process comprises: (a) reacting the 2,6-naphthalenedicarboxylic acid containing residual cobalt and manganese oxidastion catalyst comonents with methanol at an elevated temperature in the presence of a strong acid to form a reaction mixture comprising dimethyl-2,6-naphthalenedicarboxylate; (b) crystallizing the dimethyl-2,-naphthalenedicarboxylate by cooling the reaction mixture; (c) partitioning crystallized dimethyl-2,6-naphthalenedicarboxylate from reaction mixture mother liquor containing residual oxidation catalyst metals solubilized by the strong acid; (d) vacuum distilling the recrystallized dimethyl-2,6-naphthalenedicarboxylate; and (e) recovering purified dimethyl-2,6-naphthalenedicarboxylate.

Preferably, after step (c), the crystallized dimethyl-2,6-naphthalenedicarboxylate is further purified by dissolving the crystallized dimethyl-2,6-naphthalenedicarboxylate in a recrystallization solvent at an elevated temperature to form a recrystallization mixture; recrystallizing dimethyl-2,6-naphthalenedicarboxylate by cooling the recrystallization mixture; partitioning recrystallized dimethyl-2,6-naphthalenedicarboxylate from the recrystallization mother liquor; and vacuum distilling the recrystallized dimethyl-2,6-naphthalenedicarboxylate.

A large number of suitable esterificaiton catalysts are known in the art for carrying out the esterificaiton of 2,6-naphthalenedicarboxylate acid with methanol, such as, for example, molybdenum trioxide, zinc oxide, titinate esters, organo tin compounds as well as those catalysts disclosed in British Patent Specification 1,437,897. However, we hav found that a strong acid catalyst, particularly sulfuric acid, has the advantage of solubilizing the residual oxidation catalyst metals in the 2,6-NDA and, consequently, providing for their removal when the esterification reaction mother liquor is separated from the crystallized DM-2,6-NDC. Unless solubilized or otherwise removed, the oxidation catalyst metals remain with the DM-2,6-NDC. Elimination of the oxidation catalyst metals from the DM-2,6-NDC prior to distillation provides for an improved distillation step. The distillation step is required for preparing highly pure DM-2,6-NDC having low levels of particulate contaimination. By operating according to the process of this invention highly pure DM-2,6-NDC can be prepared.

DETAILED DESCRIPTION OF THE INVENTION

The 2,6-naphthalenedicarboxylate acid (2,6-NDA) used to prepare dimethyl-2,6-naphthalenedicarboxylate (DM-2,6-NDC) in the process of this invention is prepared by the liquid phase oxidation of a 2,6-dialkyl or 2-alkyl-6-acyl naphthalene feedstock compound using molecular oxygen and catalyzed by a catalyst comprising cobalt, manganese and bromine components. The alkyl group in the 2,6-dialkylnaphthalene contains one to three carbon atoms and is independently selected from methyl, ethyl and isopropyl. Thus, the 2,6-dialkylnaphthalene can, for example, be 2,6-dimethylnaphthalene, 2,6-diethylnaphthalene, 2-ethyl-6-methylnaphthalene or 2,6-diisopropylnaphthalene. The alkyl group in the 2-alkyl-6-acyl naphthalene compound is also an alkyl group containing one to three carbon atoms and is selected from methyl, ethyl and isopropyl. The acyl group in the 2-alkyl-6-acyl naphthalene compound contains two to five carbon atoms. Preferably, the acyl group is acetyl, i.e., a two carbon atom acyl group. Methods for preparing 2,6-dialkylnaphthalenes and methods for preparing 2-alkyl-6-acyl naphthalenes are well known in the art. For example, in Sikkenga et al., U.S. patent applications Ser. Nos. 539,007 and 539,087, filed Jun. 15, 1990, now abandoned and U.S. Pat. No. 5,034,561; respectively, processes for preparing 2,6-dimethylnaphthalene are disclosed; in Hagen et al., U.S. patent application Ser. No. 486,783, filed Mar. 1, 1990, now U.S. Pat. No. 5,026,917, processes for preparing 2-acyl-6-methylnaphthalene are disclosed, and in Hagen et al., U.S. Pat. No. 4,873,386, issued Oct. 10, 1989, processes for preparing 2,6-diethylnaphthalene are disclosed. 2,6-Dimethylnaphthalene and 2,6-diethylnaphthalene, because they are most easily prepared and are low in molecular weight, are the preferred oxidation feedstocks for the process of this invention.

The oxidation reaction used to convert the 2,6-dialkyl- or 2-alkyl-6-acyl naphthalene feedstock compound to 2,6-naphthalenedicarboxylic acid is a liquid phase reaction wherein a heavy metal catalyst comprising cobalt, manganese and bromine components is used to catalyze the oxidation of the alkyl groups and acyl groups on a given naphthalene compound to carboxylic acid groups. When the alkyl group is ethyl or isopropyl, a cerium catalyst component is also used. A source of molecular oxygen, such as air, supplies the oxygen for the oxidation reaction. The solvent for the liquid phase oxidation reaction comprises a low molecular weight aliphatic carboxylic acid having one to six carbon atoms, or a mixture of such a low molecular weight aliphatic carboxylic acid and water. Suitable solvents include acetic acid, propionic acid, n-butyric acid, water and mixtures thereof. Preferably, due to cost and availability, the oxidation solvent comprises acetic acid. More preferably, the solvent comprises a mixture of acetic acid and water. When water is used with acetic acid as the solvent, the water is suitably 1 to 20 weight percent relative to the acetic acid, as introduced into the oxidation reactor. During the oxidation reaction, heat is generated. This heat is dissipated in part by the vaporization of the solvent in the oxidation reactor. Typically, some of the vaporized solvent is withdrawn from the reactor, condensed, and then returned to the reactor. Additionally, some solvent is withdrawn from the oxidation reactor as a liquid in the product stream. After separation of the crude 2,6-naphthalenedicarboxylic acid from the product stream, at least a portion of the oxidation reaction mother liquor can be recycled to the oxidation reactor.

The source of molecular oxygen employed in the oxidation step of the process of this invention can vary in molecular oxygen concentration from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis).

In more detail, the catalyst employed in the oxidation step of the process of this invention comprises a bromine-containing component and a cobalt- and manganese-containing component, and can additionally comprise accelerators known in the art. The weight ratio of cobalt (calculated as elemental cobalt) in the cobalt component of the catalyst to the 2,6-dialkylnaphthalene or 2-alkyl-6-acyl naphthalene in the liquid-phase oxidation is in the range of from about 0.1 to about 500 milligram atoms (mga) per gram mole of dialkylnaphthalene or 2-alkyl-6-acyl naphthalene. The weight ratio of manganese (calculated as elemental manganese) in the manganese component of the catalyst to cobalt (calculated as elemental cobalt) in the cobalt component of the catalyst in the liquid-phase oxidation is in the range of from about 0.1 to about 10 mga per mga of cobalt. When used, the weight ratio of cerium (calculated as elemental cerium) in the cerium component of the catalyst to cobalt (calculated as elemental cobalt) in the cobalt component of the catalyst in the liquid-phase oxidation is in the range of about 0.025 to about 1.0 mga per mga of cobalt. The weight ratio of bromine (calculated as elemental bromine) in the bromine component of the catalyst to total cobalt and manganese (calculated as elemental cobalt and elemental manganese) in the cobalt and manganese components of the catalyst in the liquid-phase oxidation is in the range of from about 0.05 to about 5.0 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromide can be employed. The 0.05:1.0 to 5.0:1.0 bromine to total cobalt and manganese milligram atom ratio is provided by a suitable source of bromine. Such bromine sources include elemental bromine ($Br_2$), or ionic bromide (e.g., HBr, NaBr, KBr, $NH_4Br$, etc.), or organic bromides which are known to provide bromide ions at the at the operating temperature of the oxidation (e.g., benzylbromide, mono- and di-bromoacetic acid, bromoacetyl bromide, tetrabromoethane, ethylene dibromide, etc.). The total bromine in molecular bromine and ionic bromide is used to determine satisfaction of the elemental bromine to total cobalt and manganese milligram atom ratio of 0.05:1.0 to 5.0:1.0. The bromine ion released from the organic bromides at the oxidation operating conditions can be readily determined by known analytical means.

In operation, the minimum pressure at which the oxidation reactor is maintained is that pressure which will maintain a substantial liquid phase of the 2,6-dialkylnaphthalene or 2-alkyl-6-acyl naphthalene and at least 50 and preferably at least 70 percent of the solvent. The 2,6-dialkylnaphthalene or 2-alkyl-6-acyl naphthalene and solvent not in the liquid phase because of vaporization is removed from the oxidation reactor as a vapor-gas mixture, condensed, and then returned to the oxidation reactor. When the solvent is an acetic acid-water mixture, suitable reaction pressures in the oxidation reactor are in the range of from about 0 atmosphere absolute to about 35 atmospheres absolute, and typically are in the range of from about 10 atmospheres absolute to about 30 atmospheres absolute. The temperature range within the oxidation reactor is generally from about 120° C., preferably from about 150° C., to about 240° C., preferably to about 230° C. The solvent residence time in the oxidation reactor is generally from about 20 to about 150 minutes and preferably from about 30 to about 120 minutes.

The oxidation of the process of this invention can be performed either on a batch, continuous, or semi-continuous mode. In the batch mode, the 2,6-dialkylnaphthalene or 2-alkyl-6-acyl naphthalene, solvent and the catalyst components are initially introduced batchwise into the reactor, and the temperature and pressure of the reactor contents are then raised to the desired levels to start the oxidation reaction. Air is introduced continuously into the reactor. After commencement of the oxidation reaction—for example, after all the 2,6-dialkylnaphthalene or 2-alkyl-6-acyl naphthalene has been completely introduced into the reactor—the temperature of the reactor contents is raised.

In the continuous mode, each of 2,6-dialkylnaphthalene or 2-alkyl-6-acyl naphthalene, air, solvent and catalyst are continuously introduced into the reactor, and a product stream comprising 2,6-NDA and catalyst components dissolved in the solvent is withdrawn from the reactor. In the semicontinuous mode, the solvent and catalyst are initially introduced into the reactor and then the 2,6-dialkynaphthalene or 2-alkyl-6-acyl naphthalene and air are continuously introduced into the reactor. Catalyst can also be added during the reaction. Thereafter, the product stream in the continuous mode or the reactor contents in the batch or semicontinuous mode are cooled to a temperature in the range of from about 40° C. to about 150° C. in at least one step and in at least one crystallizer such that essentially all of the 2,6-NDA crystallizes in the solvent. Following crystallization, the resulting slurry of 2,6-NDA in the mother liquor is separated, typically by centrifugation, at a temperature in the range of from about 40° C. to about 150° C. Suitably, the separation is performed at essentially the same temperature as the final crystallization temperature. Processes for oxidizing 2,6-diethyl- and 2,6-diisopropylnaphthalene are disclosed in U.S. patent application Ser. No. 557,588 filed on Jul. 24, 1990, the specification of which is hereby specifically incorporated by reference.

After the 2,6-NDA is prepared, the next step comprises converting it, by esterification with methanol, to DM-2,6-NDC. Although some impurities such as brominated 2,6-naphthalenedicarboxylic acid and other brominated compounds, 6-formyl-2-naphthoic acid (FNA), 6-methyl-2-naphthoic acid, and cobalt and manganese catalyst metals are partly removed during the process of isolating 2,6-NDA from the oxidation reaction mixture, unacceptable levels of impurities particularly cobalt and manganese catalyst metals remain with the 2,6-NDA and are consequently carried over to the esterification reaction and must be removed during the purification of DM-2,6-NDC. Typically, the 2,6-NDA used in the process of this invention contains from about 1,000 to about 20,000 ppm, by weight, residual oxidation catalyst metals.

In the process of this invention, 2,6-NDA is converted to DM-2,6-NDC by heating 2,6-NDA with methanol at a temperature and for a time sufficient to convert at least a portion, preferably at least 75 percent and more preferably at least about 85 percent of the 2,6-NDA to DM-2,6-NDC. Although other solvents can be used along with the methanol, it is presently preferred to use only methanol. This esterification reaction generates one molecule of water for each carboxylic acid moiety esterified with methanol. The weight ratio of methanol to 2,6-NDA is suitably in the range of about 5:1 to about 20:1, preferably in the range of about 10:1, respectively. When a low ratio of methanol to 2,6-NDA is used, for example, about 5:1, relatively large amounts of the mono-methyl ester of 2,6-naphthalenedicarboxylic acid (MM-2,6-NDC) are formed in the esterification reaction. MM-2,6-NDC, which is a high melting solid, can be removed prior to the distillation step by the process disclosed in Holzhauer, et al., U.S. patent application Ser. No. 708,500 filed concurrently herewith, the specification of which is hereby specifically incorporated by reference. However, in the process of this invention, which is preferably used in smaller-scale commercial operations, it is presently preferred to use ratios of methanol to 2,6-NDA that do not produce large amounts of MM-2,6-NDC. Large amounts of MM-2,6NDC, if not removed, can precipitate in and foul the distillation apparatus used for distilling DM-2,6-NDC.

The temperature for the esterification reaction is suitably in the range of about 80° C. to about 200° C., preferably in the range of 90° C. to about 150° C. The pressure for the esterification reaction suitably ranges from about 2.0 atmospheres absolute to about 40 atmospheres absolute. Preferably, due to the low boiling point of methanol and the preferred reaction temperature of 90° C. to about 150° C., the pressure for the esterification reaction is in the range of about 3 to about 15 atmospheres absolute. It is desirable to maintain the pressure at a level sufficient to maintain at least a portion of the methanol in the liquid state.

The reactor used to carry out the esterification reaction can be any vessel or apparatus suitable for conducting the reaction at the desired reaction temperature and pressure. For example, the reactor can be a well-stirred batch reactor, a continuous flow-stirred tank reactor, with or without partitions, or a tubular reactor, preferably a plug-flow tubular reactor. The reactor can be equipped with suitable agitators and baffles to provide for adequate mixing.

The esterification reaction residence time in the esterification reactor is suitably in the range of about 0.01 to about 10 hours.

We have determined that a strong acid catalyst accelerates the esterification reaction and also solubilizes a major portion of the residual oxidation catalyst metal in the 2,6-NDA. Preferably at least about 50 weight percent, more preferably at least about 75 weight percent and most preferably at least about 90 weight percent of the oxidation catalyst metals in the 2,6-NDA are solubilized by the strong acid catalyst. Once solubilized in the esterification reaction mixture, the oxidation catalyst metals are removed with the esterification reaction mother liquor when it is partitioned from the DM-2,6-NDC product. Suitable strong acid esterification catalysts include the inorganic acids such as sulfuric acid, phosphoric acid, HF and HCl strong organic acids such as an aromatic sulfonic acid including benzene sulfonic acid, toluene sulfonic acid, sulfonic acids made by sulfonating an alkylated aromatic compound, methane sulfonic acid, and the chloro- and fluoro-acetic acids, i.e. mono-, di- and tri-chloroacetic acid, are also suitable strong acid catalysts. The amount of strong acid catalyst required for catalyzing the methanol esterification of 2,6-NDA and solubilizing a substantial portion of the residual oxidation catalyst metals is about 2 to about 25, and preferably 4 to about to 16 weight percent based on the weight of 2,6-NDA charged to the esterification reaction zone. Sulfuric acid is the preferred strong acid catalyst for the esterification reaction in the process of the invention.

The esterification reaction product mixture typically comprises a mixture of DM-2,6-NDC and, depending on the weight ratio of methanol to 2,6-NDA, various levels of MM-2,6-NDC. The esterification reaction product mixture also contains methanol, water, organic impurities, and solubilized oxidation catalyst metals. Because the DM-2,6-NDC is more soluble in methanol than 2,6-NDA, the DM-2,6-NDC is in solution in the hot esterification reaction mixture. The MM-2,6-NDC is also typically in solution.

After the esterification reaction is completed, the esterification reaction mixture is cooled to crystallize the DM-2,6-NDC contained therein. The cooling can be accomplished by any suitable means. However, the cooling is most efficiently accomplished by a pressure reduction with the consequent evaporation of methanol cooling the esterification reaction mixture. This can be accomplished in one zone, or it can be accomplished in a series of cooling zones. In a batch mode operation, the esterification reaction vessel can be used to crystallize the DM-2,6-NDC. Although the temperature to which the esterification reaction mixture is cooled is variable and depends, in part, upon the ratio of methanol to 2,6-NDA used in the esterification reaction and the desired degree to which the DM-2,6-NDC is to be crystallized from the methanol, the esterification reaction mixture is typically cooled to a temperature not greater than about 50° C., preferably to a temperature in the range of about 10° C. to about 40° C., and most preferably to a temperature of about 20° C. to about 30° C. Cooling the reaction mixture to these temperatures can be suitably accomplished by subjecting the esterification reaction mixture to a vacuum, thereby accelerating evaporative cooling and achieving temperatures below the normal boiling point of methanol. All or part of the evaporated methanol may be condensed by cooling and returned to the crystallization vessel. Other suitable methods for cooling the mixture can be used, however, such as using cooling coils cooled by chilled water. Cooling the reaction mixture to these temperatures assures that a major portion of the DM-2,6-NDC crystallizes from solution. Preferably at least about 75 percent and more preferably at least about 90 percent of the DM-2,6-NDC in the esterification reaction mixture crystallizes from solution.

After the DM-2,6-NDC crystallizes, it is partitioned from the esterification reaction mother liquor. This can be accomplished by any suitable means for partitioning solids from liquids such as filtration, centrifugation or settling. Unreacted 2,6-naphthalenedicarboxylic acid and MM-2,6-NDC also typically precipitate during the cooling and are collected with the DM-2,6-NDC.

With the esterification reaction mother liquor are rejected most of the impurities such as brominated products, esterified FNA, solubized catalyst metals, water produced in the esterification reaction, and yet unidentified oxidation and esterification reaction intermediates and reaction side products. The esterification reaction mother liquor is, however, mainly unreacted methanol used for the esterification reaction. This methanol can be recovered from the mother liquor and used for recycle to one or more of the other process steps.

As previously mentioned, if the oxidation catalyst metals are permitted to remain in the DM-2,6-NDC purification process stream, they concentrate in either the distillation bottoms, and, if the DM-2,6-NDC is injected into the distillation column at a point within the distillation column packing, the oxidation catalyst metals will rapidly and possibly irreversibly plug the distillation column. Also, when oxidation catalyst metals are allowed to concentrate in the distillation bottoms, they can produce a highly viscous material that is not easily removed by, for example, a purge stream. Periodic cleaning would therefore necessitate the discontinuance of the distillation process. Therefore, these catalyst metals must be removed in order to provide for the efficient distillation of DM-2,6-NDC. Furthermore, it is desirable to recycle to the esterification reactor at least part and preferably substantially all of the distillation bottoms to recover any DM-2,6-NDC and/or MM-2,6-NDC contained therein. If the catalyst metals are not removed, they will only increase in concentration in the distillation bottoms with recycle and aggravate the aforementioned problems.

Crystallized DM-2,6-NDC collected by filtration, centrifugation, or that obtained from some other means used for partitioning the crystallized product from the esterification reaction mother liquor, is preferably washed with methanol, mixtures of methanol and water, or other suitable solvent such as a $C_5$-$C_{10}$ hydrocarbon, i.e., pentanes, hexanes, toluene, xylenes, cyclohexane, etc. A $C_6$-$C_{10}$ halogenated aromatic such as chlorobenzene, or a $C_1$-$C_4$ carboxylic acid such as acetic and propionic acid, and mixtures of these acids with water are also suitable solvents for washing the crystallized esters. This washing step removes additional impurities and results in purer DM-2,6-NDC, particularly if the solvent used to wash the DM-2,6-NDC is at an elevated temperature. Most preferably, the solvent used to wash the crystallized DM-2,6-NDC is methanol, or a mixture of methanol and water. The weight ratio of solvent, preferably methanol or methanol/water mixture, to the DM-2,6-NDC used for washing is in the range of about 0.2:1 to about 2:1, respectively.

The crystallized DM-2,6-NDC is preferably subjected to a recrystallization procedure for further purification. Recrystallization is accomplished by contacting the DM-2,6-NDC with methanol or other suitable recrystallization solvent and maintaining the resulting recrystallization mixture at an elevated temperature to dissolve at least a portion of the DM-2,6-NDC and preferably at least about 75 percent and more preferably at least about 90 percent of the DM-2,6-NDC. A pressure vessel can be used to heat the mixture to a temperature above the normal boiling point of the solvent. A suitable weight ratio of recrystallization solvent to DM-2,6-NDC is in the range of about 1:1 to about 10:1, and preferably about 2:1 to about 6:1, respectively. Methanol is the presently preferred recrystallization solvent because it is used in the esterification reaction and it can be treated and recycled along with other methanol process streams. These amounts of methanol are generally sufficient to dissolve the DM-2,6-NDC at reasonable temperatures and provide a recrystallized product suitable for the next stage of purification. However, as mentioned above, other recrystallization solvents are suitable. For example, $C_6$-$C_{10}$ aromatic solvents such as benzene, toluene, o-, m- or p-xylene, a mixture of xylenes, ethylbenzene, cumene, pseudocumene, and the like, are also suitable as recrystallization solvents. Halogenated $C_6$-$C_{10}$ aromatic compounds such as chlorobenzene are also suitable. The xylenes are particularly preferred aromatic recrystallization solvents. The preferred temperature for dissolving the DM-2,6-NDC in the recrystallization solvent is in the range of about 80° C. to about 190° C.

After the DM-2,6-NDC and the recrystallization solvent are maintained at an elevated temperature so that at least a portion of the DM-2,6-NDC is dissolved, the resulting mixture is cooled to a recrystallization temperature to recrystallize the dissolved DM-2,6-NDC. Cooling is accomplished by any suitable means such as using cooling coils within the vessel used for the recrystallization. However, it is preferable from the standpoint of cost in a plant operation to reduce the pressure and allow the mixture to cool by evaporative cooling. If the dissolution of the DM-2,6-NDC in the recrystallization solvent is accomplished at temperatures above the normal boiling point of the recrystallization solvent, the pressure need only be reduced to lower the temperature of the mixture to the desired recrystallization temperature. However, attaining temperatures below the normal boiling point of the solvent by evaporative cooling requires the application of a vacuum to the vessel or apparatus holding the recrystallization solution. The recrystallization temperature is any temperature that allows for the recrystallization of at least a portion of the DM-2,6-NDC. Preferably, the recrystallization temperature is not greater than about 50° C., more preferably in the range of about 10° C. to about 40° C. and most preferably about 20° C. to about 30° C.

Upon recrystallization of the solid DM-2,6-NDC, it is partitioned from the recrystallization solvent (mother liquor) by any suitable means for partitioning solids from liquids such as, for example, settling, centrifugation, vacuum or pressure filtration, etc. If methanol is used as a solvent, the filtrate can be recycled to the esterification reactor. Alternatively, it can be treated to remove the methanol and the remaining heavies can be recycled to the esterification reactor or discarded. If a solvent other than methanol is used as the recrystallization solvent, it too can be treated to remove heavies and then purified for reuse. Solid recrystallized DM-2,6-NDC collected on the filter, centrifuge, etc. is preferably washed, preferably with the solvent used for the recrystallization step, or other suitable solvent such as those discussed hereinabove used to wash the crystallized DM-2,6-NDC. Washing removes additional impurities particularly if the washing solvent is at an elevated temperature. The weight ratio of solvent to DM-2,6-NDC used to wash the recrystallized DM-2,6-NDC is suitably in the range of about 0.2:1 to about 2:1, respectively. Depending on variables such as the amount of time the DM-2,6-NDC remains in the centrifuge, vacuum filter, pressure filter or other partitioning device, the pressure (or vacuum) applied, and the solvent used for recrystallization and/or washing, etc., the DM-2,6-NDC filter cake will contain variable amounts of solvent. This solvent can, if desired, be removed by one or more drying techniques such as heating in a sweep of air or inert gas, use of a vacuum with or without additional heating, or other suitable means for drying the DM-2,6-NDC. Presently preferred, however, is to heat the DM-2,6-NDC, optionally at reduced pressure, until it becomes molten and simultaneously distilling any excess solvent from the DM-2,6-NDC. Molten DM-2,6-NDC, preferably free of substantially all of the solvent used for the recrystallization and/or washing, is distilled in the next step of the process. Although only one recrystallization step has been described, it will be apparent to those of skill in the art that, depending on the degree of purity required, one or more additional recrystallization procedures, with or without a washing step and using the same or different recrystallization and washing solvents, can be used. Additionally, while the DM-2,6-NDC is in solution in the recrystallization solvent, it can be treated with one or more physical or chemical means for stabilizing the DM-2,6-NDC or for removing impurities. For example, it can be treated with an oxidizing agent such as air, a peroxide, hydroperoxide or peracid. It can be treated with a reducing agent. It can also be treated with a base such as an alkoxide, e.g., sodium methoxide, or calcium, sodium or potassium hydroxide, carbonate or bicarbonate. Sodium methoxide provides for superior color DM-2,6-NDC when added in an amount of about 0.1 to about 2 weight percent based on the weight of DM-2,6-NDC in the recrystallization solvent.

Molten crystallized, or recrystallized ester is distilled in at least one distillation step. Due to the high melting point of DM-2,6-NDC (approximately 190° C.), the temperature of the distillation is necessarily above about 190° C. Also, because DM-2,6-NDC deteriorates in purity, and particularly in color, by being maintained at excessive temperatures, it is preferable to conduct the distillation at reduced pressure. Distillation tower bottoms are therefore suitably in the range of about 190° C. to about 310° C., preferably about 210° C. to about 290° C. Distillation pressure can range from about 2.5 torr to about 200 torr. Preferably, the distillation pressure is in the range of about 6 to about 100 torr.

The distillation can be a simple distillation, however, to attain the highest purity of DM-2,6-NDC, it is preferable to use a fractionating column. The fractionating column can be packed with random or structured column packing designed to increase the liquid-vapor contact in the column. Fractionation columns having trays, e.g. sieve trays or bubble cap trays, which are well known in the distillation art, are also suitable.

Distillation of the DM-2,6-NDC removes undesirable heavy high boiling impurities, such as residual MM-2,6-NDC, various colored by-products, and residual catalyst metals. Importantly, the distillation removes particulate contaminants from the DM-2,6-NDC. Particulate contaminants are difficult to remove from the DM-2,6-NDC unless a distillation step is employed. For example, even if the DM-2,6-NDC is dissolved in a suitable solvent, filtered and recrystallized, the solid DM-2,6-NDC must be collected by, for example, filtration or centrifugation and is also usually dried to free the DM-2,6-NDC of excess recrystallization solvent. These operations introduce particulate contaminants to the DM-2,6-NDC. Consequently, the distillation procedure of this invention as the final purification procedure assures that the DM-2,6-NDC contains low levels of particulate contaminants, levels that are suitable for manufacturing PEN that can be used for fabricating high quality thin films. Preferably, the distillation step provides for DM-2,6-NDC containing less than about 5000 and more preferably less than about 2000 particles greater than about 1.5 microns in size per gram of DM-2,6-NDC as measured by a HIAC/ROYCO particle analyzer instrument.

The distilled molten DM-2,6-NDC is optionally cooled and solidified in a suitable apparatus such as a flaker.

It is to be understood that the hereinabove described process for preparing purified DM-2,6-NDC can be conducted such that each process step is operated in either a batch or continuous manner.

The following examples are being presented to facilitate an understanding of the process of the present invention without intending to limit the scope thereof.

In the following Examples, "MeFNA" is the methyl ester of 2-formul-6-naphthoic acid.

YIE measurements and APHA color measurements were used to evaluate the color of DM-2,6-NDC. "Ambient" YIE values for the samples of DM-2,6-NDC were measured on a Gardner XL-835 tri-stimulus colorimeter using quartz sample cells. YIE measurements were taken on a 0.75 gram sample of DM-2,6-NDC dissolved in 25 ml. of chloroform (see ASTM method E-313, "Indexes of Whiteness and Yellowness of Near-White, Opaque Materials"). YIE values referred to as "Air Melt" were similarly measured using samples that were first maintained at 235° C. for six hours in a glass vessel without excluding air, i.e., the "Air Melt" measurements are an indication of the stability of the DM-2,6-NDC sample to air at an evaluate temperature.

APHA (American Public Health Assoc.) color values were measured using molten samples of DM-2,6-NDC.

Delta Y values were measured by passing a solution of 20 g of DM-2,6-NDC in 1000 ml of dichloromethane through 47 mm diameter filter paper and measuring the "Y" value of the filter paper using a Gardner XL-835 tri-stimulus colorimeter. Delta Y is a measure of particulate contamination in the DM-2,6-NDC.

Particulate contamination the DM-2,6-NDC was also measured using a HIAC/ROYCO particle analyzer. A methylene chloride solution of DM-2,6-NDC was used for the measurements. This particle analyzer measures particles greater than 1.5 microns in size.

EXAMPLE I

Crude 2,6-NDA was esterified with methanol utilizing sulfuric acid catalyst in a batch process. The 2,6-NDA was prepared by the cobalt, manganese and bromine catalyzed liquid-phase oxidation of 2,6-dimethylnaphthalene. A glass-lined reactor was charged with 130 parts crude 2,6-NDA as a slurry in 1140 parts methanol and 13 parts, 80 percent sulfuric acid. (The other 20% is water.) The reactor was equipped with an overhead condenser and 150 psig rupture disc. The mixture was heated, utilizing a steam jacket, until the reactor internals reached approximately 120° C. The esterification mixture was maintained at 120° C. for a six hour period after which the reactor was slowly cooled overnight with a water jacket. The crude ester was isolated from the mother liquor using a perforated basket centrifuge. The product was isolated in four separate centrifuge cycles and each centrifuge cake was washed with 50 parts methanol. The crude ester (minus 10 parts for sample retain) was recrystallized in 1050 parts methanol in the same glass-lined reactor. The mixture was heated until dissolution, held at 120° C. for 30 minutes and slowly cooled to ambient temperature overnight. The recrystallized DM-2,6-NDC was isolated in three centrifuge cycles and washed with 50 parts methanol. The wet recrystallized cake was dried in an explosion-proof tray oven. A summary of the analyses of the crude 2,6-NDA, crude DM-2,6-NDC, and recrystallized DM-2,6-NDC (131 parts) is presented in Table I.

The recrystallized material was purified by batch distillation. The apparatus consisted of a heated one-liter reboiler flask; a 1" ID column filled with 34" of a high-efficiency structured gauze packing; an overhead condenser cooled with tempered oil; a reflux splitter; a condensate receiver; and a vacuum pump protected by a water-cooled cold trap. The product takeoff system was enclosed in a box heated to about 230° C. to prevent freezing of the distillate.

Prior to the distillation, the unit was washed with boiling xylene. Dry recrystallized DM-2,6-NDC (493.2 g) was then distilled at a pressure of 20 torr. The product was recovered as three fractions weighing 157.6; 157.7; and 123.7 grams, respectively. The water trap contained 0.50 gram of solid material. A distillation pot residue of water-like fluidity with no visible solids and weighing 17.74 g (3.60 percent of the feed) was obtained. The total recovery was 92.7 weight percent based on the feed. Typically about 5-10 percent of the charge is held up in the distillation unit, presumably mostly in the packing.

Table II shows that the product was of excellent quality. There was no detectable sulfur in the product, not even in the first cut. The trap material contained 40 ppm sulfur, but its contribution on a weight basis is very small. The acidity of all distillates was extremely low. Bromine, organic contaminants, and color were very low. Importantly, the use of sulfuric acid as the catalyst for the esterification provided for the removal of oxidation catalyst metals resulting in the fluid, solids-free distillation pot residue. The low ash level of the DM-2,6-NDC relative to the ash level in the 2,6-NDA demonstrates that most of the catalyst metals are removed by the esterification process of this invention.

TABLE 1

Analytical Results for Crude 2,6-NDA Esterification and Recrystallization

|  | 2,6-NDA | Crude DM-2,6-NDC | Recrystallized DM-2,6-NDC |
|---|---|---|---|
| FNA$^a$ (ppm)$^b$ | 5212 | ND | ND |
| MeFNA$^a$ (ppm) | NA | 296 | 29 |
| MM-2,6-NDC$^a$ (ppm) | NA | 11000 | 1795 |
| 2,6-NDA (ppm) | NA | ND | ND |
| Bromine$^c$ (ppm) | 1264 | 40 | 15 |
| Ash$^d$ (ppm) | 1585 | 10 | 10 |
| Sulfur$^e$ (ppm) | NA | 67 | 31 |
| Acid Number (mg KOH/gram) | NA | 2.97 | 0.05 |

NA = Not Applicable
ND = Not Detected
$^a$Determined by liquid chromatography.
$^b$Parts per million
$^c$Determined by x-ray fluorescence.
$^d$Measure of metal content.
$^e$Determined couloumbmetrically.

TABLE II

Batch Distillation Results

| Sample | Feed | Dist. Cuts 1-3 | Dist. Cuts 4-6 | Dist. Cuts 7-9 | Total Dist. | Bottoms | Trap |
|---|---|---|---|---|---|---|---|
| Sample Wt., g | 493.2 | 157.6 | 157.7 | 123.7 | 439.0 | 17.74 | 0.50 |
| CONC.$^a$ ppm: |  |  |  |  |  |  |  |
| Br | 15 | 5 | <2 | <2 | <3 | 127 | NA |
| Co | <2 | <2 | <2 | <2 | <2 | 104 | NA |
| Fe | <2 | <2 | <2 | <2 | <2 | 61 | NA |
| Mn | <2 | <2 | <2 | <2 | <2 | 63 | NA |
| Sulfur,$^b$ ppm | 31 | <1 | <1 | <1 | <1 | NA | 40 |
| YIE (Ambient) | NA | 0.02 | 0.01 | 0.01 | 0.01 | NA | NA |
| YIE (Air Melt) | 27.2 | 0.19 | 0.17 | 0.13 | 0.17 | NA | NA |
| Delta Y | NA | 1.62 | 0.84 | 0.29 | 0.97 | NA | NA |
| Acid No. mg KOH/g | 0.050 | 0.01 | <0.01 | <0.01 | <0.01 | NA | NA |
| GC.$^c$ ppm: |  |  |  |  |  |  |  |
| MeFNA | NA | 40 | <20 | <20 | <27 | NA | NA |
| Unknowns | NA | 90 | <20 | <20 | <45 | NA | NA |
| LC.$^d$ ppm: |  |  |  |  |  |  |  |
| 2,6-NDA |  | 4 | 2 | 4 | 3 | 2450 | NA |
| MM-2,6-NDC | 1800 | 3 | 1 | 3 | 2 | 67,300 | NA |
| MeFNA | 29 | 48 | 10 | 8 | 23 | 43 | NA |

NA = Not Available
$^a$Determined by X-ray fluorescence.
$^b$Determined couloumbmetrically.
$^c$Gas chromatography, parts per million by weight.
$^d$Liquid chromatography, parts per million by weight.

EXAMPLE II

According to the procedure of Example I, crude 2,6-naphthalenedicarboxylic acid (2,6-NDA) was esterified, and the resulting crude dimethyl-2,6-naphthalenedicarboxylate (DM 2,6-NDC) was recrystallized and dried.

The recrystallized material was purified by continuous distillation. The apparatus consisted of a heated feed tank on a scale, a feed control valve, a 3" ID column filled with 78" of Sulzer CY TM packing; a wiped-film evaporator; a residue receiver, a reflux splitter, an overhead condenser cooled with tempered oil, a condensate receiver, and a vacuum pump protected by two cold traps. The column and the product takeoff system were enclosed in an insulated box heated to about 230° C. to prevent freezing of the distillate.

The feed was introduced above the evaporator and below the packing at a rate of 60.5 g/min. The reflux ratio was 1:1; and the pressure at the reflux splitter was maintained at 20 torr. The average distillate and residue rates were about 43.9 and 16.6 g/min., respectively. Table III shows the product analyses. Product colors by both the YIE and APHA methods were very low. Particulate contents measured by the HIAC-Royco instrument were also very low. DM-2,6-NDC prepared by procedures similar to that used to prepare the feed DM-2,6-NDC for this example as well as by other procedures were also measured for particulate levels prior to distillation. The particulate concentrations for these samples ranged from 46,900 particles/gram to 175,000 particles/gram. Therefore, this example demonstrates that distillation effectively removes most of the particulate contamination in DM-2,6-NDC.

dures were not used to remove these metals from the esterification reaction mixture. In similar distillations, such as Example I, where the metals were not present in the distillation feed because sulfuric acid was used as an esterification catalyst, the highly viscous bottoms residue did not form.

EXAMPLE IV

Crude 2,6-NDA was esterified according to the procedure of Example I. The resulting crude DM-2,6-NDC (21 parts) was reslurried and washed with 42 parts xylene on a "Sparkler" plate filter. This cake was dissolved in 105 parts xylene at 130° C. The mixture was

TABLE III

| | Continuous Distillation of Methanol-Recrystallized DM 2,6-NDC | | | | | | |
|---|---|---|---|---|---|---|---|
| Cut No. | (Feed) | 1 | 2 | 3 | 4 | 5 | 6 |
| Br$^a$, ppm | 11 | <2 | <2 | <2 | NA | <2 | <2 |
| APHA Color | NA | 51 | 62 | 86 | NA | 72 | 62 |
| Delta Y | NA | 0.5 | 0.3 | 0.3 | NA | 0.3 | 0.9 |
| Haze (NTU) | NA | 0.04 | 0.05 | 0.04 | NA | 0.05 | 0.04 |
| YIE (Air Melt) | NA | 0.10 | 0.08 | 0.11 | NA | 0.10 | 0.08 |
| Acid No. mg KOH/g | NA | <0.01 | <0.01 | <0.01 | NA | <0.01 | 0.01 |
| Particles >1.5 microns$^b$ | NA | 1837 | 1625 | 839 | NA | 676 | 1391 |
| LC, ppm: | | | | | | | |
| 2,6-NDA | NA | <4 | <4 | <4 | NA | <4 | <4 |
| MM 2,6-NDA | 785 | 2 | 2 | 4 | NA | <2 | 4 |
| MeFNA | ND | 17 | 15 | 14 | NA | 17 | 19 |

NA = Not Available
$^a$Determined by X-ray fluorescence.
$^b$Particles greater than 1.5 microns in size per gram of DM-2,6-NDC, measured with a HIAC/ROYCO instrument.

EXAMPLE III

Recrystallized DM-2,6-NDC containing 2.28 percent 2,6-NDA, 3.53 percent MM-2,6-NDC, 0.053 percent cobalt, 0.78 percent manganese and 0.048 percent molybdenum was batch distilled at 20 torr. Molybdenum trioxide rather than a strong acid catalyst was used to prepare the DM-2,6-NDC. The distillation was terminated when the bottoms temperature reached 288° C. (i.e. 30° C. above the boiling point of pure DM-2,6-NDC at 20 torr.). At this point, 82.3 percent of the feed had distilled over, and 17.8 percent of the feed was recovered as bottoms. The material in the bottoms was a semi-solid that did not flow even at 315° C. The viscosity, measured with a Brookfield instrument, exceeded 2,000,000 cps. A material of this viscosity could not be pumped except with an extruder or similar device. The formation of this material in the distillation bottoms is, therefore, unacceptable for commercial operations. The cobalt, manganese and molybdenum in the feed for this distillation was present because procecooled at 22° C. to crystallize the DM 2,6-NDC, and the resulting slurry was separated in the plate filter. The filter cake was washed with 20 parts xylene. The washed cake was dried in a vacuum oven at 80° C.

The dried product was continuously distilled according to the procedure of Example II. The feed rate was 60.5 g/min. The reflux ratio was 1:1; and the pressure at the reflux splitter was maintained at 20 torr. The average distillate and residue rates were about 50.7 and 9.8 g/min, respectively. Table IV shows the product analyses. Product colors by both the YIE and APHA methods were very low. Particulate contents measured by the HIAC/ROYCO instrument were very low.

This example demonstrates the effectiveness of the present invention for producing purified DM-2,6-NDC. It also demonstrates that xylene is a suitable recrystallization solvent.

TABLE IV

| | Continuous Distillation of Xylene-Recrystallized DM-2,6-NDC | | | | | | |
|---|---|---|---|---|---|---|---|
| Cut No. | (Feed) | 1 | 2 | 3 | 4 | 5 | 6 |
| Br$^a$, ppm | 11 | <2 | <2 | <2 | NA | <2 | <2 |
| APHA Color | NA | 51 | 62 | 86 | NA | 72 | 62 |
| Delta Y | NA | 0.5 | 0.3 | 0.3 | NA | 0.3 | 0.9 |
| Haze (NTU) | NA | 0.04 | 0.05 | 0.04 | NA | 0.05 | 0.04 |
| YIE (Air Melt) | NA | 0.10 | 0.08 | 0.11 | NA | 0.10 | 0.08 |
| Acid No. mg KOH/g | NA | <0.01 | <0.01 | <0.01 | NA | <0.01 | 0.01 |
| Particles >1.5 microns$^b$ | NA | 1837 | 1625 | 839 | NA | 676 | 1391 |
| LC, ppm: | | | | | | | |
| 2,6-NDA | NA | <4 | <4 | <4 | NA | <4 | <4 |
| MM 2,6-NDA | 785 | 2 | 2 | 4 | NA | <2 | 4 |
| MeFNA | ND | 17 | 15 | 14 | NA | 17 | 19 |

NA = Not Available
$^a$Determined by X-ray fluorescence.
$^b$Particles greater than 1.5 microns in size per gram of DM-2,6-NDC, measured with a HIAC/ROYCO instrument.

We claim:
1. A process for preparing purified dimethyl-2,6-naphthalenedicarboxylate from 2,6-naphthalenedicar- boxylic acid, wherein the 2,6-naphthalenedicarboxylic acid is prepared by the liquid phase oxidation of a 2,6-dialkyl or 2-alkyl-6-acyl naphthalene compound using a catalyst comprising cobalt and manganese oxidation metals, which process comprises:

(a) reacting the 2,6-naphthalenedicarboxylic acid containing residual cobalt and manganese oxidation catalyst metals with methanol at a temperature in the range of about 80° C. to about 200° C., in the presence of a strong acid selected from sulfuric acid, hydrofluoric acid, hydrochloric acid, phosphoric acid, benzene sulfonic acid, alkylaromatic sulfonic acid, methane sulfuric acid, a chloroacetic acid, and a fluoroacetic acid to form a reaction mixture comprising dimethyl-2,6-naphthalenedicarboxylate;

(b) crystallizing the dimethyl-2,6-naphthalenedicarboxylate by cooling the reaction mixture;

(c) partitioning crystallized dimethyl-2,6-naphthalenedicarboxylate from reaction mixture mother liquor containing solubilized residual oxidation catalyst metals;

(d) dissolving the crystallized dimethyl-2,6-naphthalenedicarboxylate in a recrystallization solvent at a temperature in the range of about 80° C. to about 190° C., to form a recrystallization mixture;

(e) recrystallizing dimethyl-2,6-naphthalenedicarboxylate by cooling the recrystallization mixture;

(f) partitioning recrystallized dimethyl-2,6-naphthalenedicarboxylate from recrystallization mother liquor;

(g) vacuum distilling the recrystallized dimethyl-2,6-naphthalenedicarboxylate such that the distilled dimethyl-2,6-naphthalenedicarboxylate contains less than about 5000 particles greater than about 1.5 microns in size per gram of distilled dimethyl-2,6-naphthalenedicarboxylate; and (h) recovering the distilled dimethyl-2,6-naphthalenedicarboxylate.

2. The process of claim 1 wherein in the strong acid is present in an amount of about 2 to about 25 weight percent based on the weight of 2,6-naphthalenedicarboxylic acid.

3. The process of claim 1 wherein in step (b) the reaction mixture is cooled to a temperature not greater than about 50° C. to crystallize the DM-2,6-NDC.

4. The process of claim 1 wherein in step (e) the recrystallization mixture is cooled to a temperature not greater than about 50° C.

5. The process of claim 1 wherein the recrystallization solvent is methanol, a $C_6$–$C_{10}$ aromatic or a halogenated $C_6$–$C_{10}$ aromatic.

6. The process of claim 1 wherein after step (c) the crystallized dimethyl-2,6-naphthalenedicarboxylate is washed with a solvent.

7. The process of claim 1 wherein after step (f) the partitioned recrystallized dimethyl-2,6-naphthalenedicarboxylate is washed with a solvent.

8. The process of claim 1 wherein the vacuum distillation is conducted using a fractionation column.

9. The process of claim 2 wherein said strong acid is sulfuric acid.

10. The process of claim 8 wherein the fractionation column is packed with a structured packing.

11. The process of claim 1 wherein in step (d) the recrystallization mother liquor is treated with sodium methoxide.

* * * * *

UNITED STATES PATENT AND TRADEMARK OFFICE
CERTIFICATE OF CORRECTION

PATENT NO. : 5,254,719  
DATED : Oct. 19, 1993  
INVENTOR(S) : Juergen K. Holzhauer, et al Page 1 of 2

It is certified that error appears in the above-indentified patent and that said Letters Patent is hereby corrected as shown below:

| Col. | Line | |
|---|---|---|
| 3 | 23 | "oxidastion" should read --oxidation-- |
| 3 | 54 | "hav" should read --have-- |
| 4 | 4 | "2,6-naphthalenedicarboxylate acid" should read --2,6-naphthalenedicarboxylic acid-- |
| 7 | 14 | "in the range of about 10:1," should read --in the range of about 6:1 to about 10:1,-- |
| 8 | 1 | "HCl strong" should read --HCI. Strong-- |
| 12 | 33 | "evaluate temperature." should read --elevated temperature.-- |
| 15 | 59 | in Table IV, under the column "Cut No." patent reads "MM 2,6-NDA" should read --MM 2,6-NDC-- |
| 17 | 10 | "selected from sulfuric" should read --selected from the group consisting of sulfuric-- |

UNITED STATES PATENT AND TRADEMARK OFFICE
CERTIFICATE OF CORRECTION

PATENT NO. : 5,254,719
DATED : Oct. 19, 1993
INVENTOR(S) : Juergen K. Holzhauer, et al It is certified that error appears in the above-indentified patent and that said Letters Patent is hereby corrected as shown below:

| Col. | Line | |
|------|------|---|
| 17 | 13 | "methane sulfuric acid," should read --methane sulfonic acid,-- |

Signed and Sealed this

Thirtieth Day of January, 1996

Attest:

BRUCE LEHMAN

Attesting Officer

Commissioner of Patents and Trademarks